(12) United States Patent
Goldman et al.

(10) Patent No.: US 6,421,614 B1
(45) Date of Patent: Jul. 16, 2002

(54) PHOTOMETER SYSTEM FOR OBTAINING RELIABLE DATA

(76) Inventors: Donald S. Goldman, 9477 Greenback La., Suite 521, Folsom, CA (US) 95630; Nelson Wayne Lytle, 3705 W. Wackerly St., Midland, MI (US) 48640

( * ) Notice: Subject to any disclaimer, the term of this patent is extended or adjusted under 35 U.S.C. 154(b) by 0 days.

(21) Appl. No.: 09/361,090

(22) Filed: Jul. 26, 1999

(51) Int. Cl.[7] .............................................. G01N 21/00
(52) U.S. Cl. .............................. 702/32; 702/30; 702/23; 356/73
(58) Field of Search ............................. 702/72, 23, 30, 702/32; 250/339.07, 339.09, 252.1; 356/73

(56) References Cited

U.S. PATENT DOCUMENTS

| | | | |
|---|---|---|---|
| 4,975,581 A | * 12/1990 | Robinson et al. | 250/339 |
| 5,532,823 A | 7/1996 | Fukui et al. | |
| 5,592,402 A | 1/1997 | Beebe et al. | |
| 5,606,164 A | * 2/1997 | Price et al. | 250/339.09 |
| 5,610,836 A | * 3/1997 | Alsmeyer et al. | 364/498 |
| 5,706,092 A | 1/1998 | Stannard et al. | |
| 5,715,058 A | 2/1998 | Bohnert et al. | |
| 5,825,478 A | * 10/1998 | Wilcox et al. | 356/73 |

* cited by examiner

Primary Examiner—Marc S. Hoff
Assistant Examiner—Paul Kim
(74) Attorney, Agent, or Firm—Theodore J. Bielen, Jr.

(57) ABSTRACT

A system for obtaining reliable data from a chemical sample for at least one variable environmental condition utilizing a photometer. The photometer obtains sample characteristic data at a plurality of discrete wavelengths. The reliability of the data is determined by obtaining a training set of data, and obtaining a number representing the variation between the mean center of the training set of data and the data representing the sample characteristic obtained by the photometer. Such number represents the basis of determining outliers of the data representative of the reliability of the data.

20 Claims, 2 Drawing Sheets

O = LAB, GRAB SAMPLE ical measurements are typically obtained with
respect to on-line chemical processes to maintain proper
control of the same. Such measurements are also extremely
important to ascertain the reliability of such measurements.
Multivariate models are routinely used to calibrate on-line
analyzers, particularly near infrared (NIR) process
spectrometers, that acquire a spectrum of contiguous wavelength. If a chemical sample falls outside the range of
conditions of a multivariate model or when an unmodeled
interference enters into the system, analytical measurements
become biased. In certain cases such biased measurements
may constitute an error, commonly referred to as an "outlier".

All analytical instruments and methods are classified
according to the type of data provided. Instruments that
provide single data points, such as pH meters or single
wavelength filter photometers are classified as zero-order
instruments. A single value provided by these instruments is
considered a zero-order tensor. Generally, it is not possible
to detect the occurrence of an interference on a zero-order
instrument. On the other hand, first order instruments, which
obtain multiple input data points can detect occurrences of
an interference or "upset". Such first order instruments
include spectrometers, chromatographs and arrays of zero-order sensors. It should be noted that process NIR spectrometers employ entire or partial continuous spectra rather
than single analytical wavelengths. Such instruments,
although successful in obtaining data are elaborate and
expensive when compared to photometers which analyze a
set number of discrete or narrow width wavelengths.
"Upsets" have been detected in continuous spectra spectrometers through a variety of descriptive statistics that can
be calculated from a continuous spectrum. Such statistics
provide the user of the instrument with a measure of
confidence in the result.

Two important descriptive statistics employed with full or
continuous spectrum instruments are the sum of squares, Q,
and Mahalanobis distance, M. Generally, low values for Q
or M indicates a good analytical result. To indicate when
there are problems in the analysis, it is necessary to determine limits that indicate when a spectrum no longer fits the
chemometric model, e.g. an outlier.

U.S. Pat. No. 5,715,058 shows a method and device for
the optical determination of a physical quantity by deriving
a two phase-shifted signal from a common optical channel.

U.S. Pat. No. 5,532,823 teaches a method of measuring
optical characteristics of a liquid crystal cell using polarized
light.

U.S. Pat. No. 5,706,092 teaches a differential spectrometry system which detects very narrow band spectral features
by the use of optical interference filters. The detector outputs
are differenced by an operational amplifier to cancel detector
signals resulting from spectral features, to both detectors.

U.S. Pat. No. 5,606,164 shows a method and apparatus for
measuring the concentration of a fluid in a chemical process
by the application NIR to a flow cell. Light may be directed
through a chopper wheel to make both light and dark
measurements. In addition, modulated light could be passed
through a filter wheel prior to transmission to through the
flow cell. In addition, light may be directed from a plurality
of narrow band width NIR sources which is a plurality of
diodes. The data obtained may be processed to determine
outliers using the Mahalanobis distance or Robust distance.
Calibration data is obtained to compensate for spectral
artifacts.

U.S. Pat. No. 5,592,402 describes a method for interpreting complex data from detecting instrumentation such as a
chromatogram or a spectrum. The determination of any
outlier data includes the first step of calculating the average
calibration residual spectrum through an analysis technique
the residual spectrum is characterized by a single value such
that data may be classified as an outlier.

A system which is capable of producing outlier determination of data from a fixed wavelength filter photometer
would be a remarkable advance in the field of chemical
analyses.

SUMMARY OF THE INVENTION

In accordance with the present invention a novel and
useful system for obtaining reliable chemometric data from
sample is herein provided.

The system of the present invention utilizes a photometer,
including a fixed filter type, a moving filter type, a dispersive
type, as those possessing a prism or grating, and the like. In
any case, a photometer employing a plurality of independent
analytical narrow band wavelengths to analyze a sample,
such as one which would be detected in an on-line chemical
process, may be used herein. Reference is made to U.S. Pat.
No. 5,825,478 which shows a multifunctional fixed filter
photometer apparatus which would be suitable in the system
of the present invention. It has been found that such a fixed
wavelength filter photometer performs on-line analyses
which are considered to be a difficult task for analytical
instruments. The particular photometer shown in U.S. Pat.
No. 5,825,478 uses a plurality of independent analytical
wavelengths derived from a broad band source of light by
the use of narrow bandwidth interference filters. Thus, this
instrument is considered to be a first order instrument and
may be used to obtain data to ascertain a sample
characteristics, such as absorbance, fluorescence, turbidity,
optical density, and others. It is well known that absorbance
is directly related to concentration and may be employed to
that end. Thus, through at least first and second wavelengths,
each possessing a narrow bandwidth, photometric data may
be obtained from a chemical sample.

Also, in the present invention, means is provided for
determining the reliability of the data obtained by the fixed
filter photometer. Such means may take the form of a
utilizing such fixed filter photometer or utilizing other
chemical analyses to produce a training set of data representing a sample characteristic, such as color, specific
chemical component, and the like, by using multiple wavelengths to analyze the sample. Also, certain sample
characteristics, such as temperature, pressure, contaminant
concentration, and the like are varied. At this point, a
calibration set is established in which a multivariate method
such as principal components analysis (PCA), principal
components regression (PCR), partial least squares (PLS), or
multiple linear regression (MLR) is employed. The variation
in the data is explained by factors or principal components
(PC). Mathematically, these techniques rely on the eigenvector decomposition of the covariance or correlation matrix
of the data set. The eigenvector may be calculated mathematically or through PCA on the mean centered data set.

Essentially, the eigenvector is comprised variables measured on a data set which can be made to lie in a plane.

The identification of outliers is obtained by calculating either the sum of squares (Q) or the Mahalanobis distance (M) on the training set of data. Other types of analyses may be used to obtain outliers, such as F-test, F-ratio, and the like. Either of these types of statistics provide a measure of confidence in subsequent measurements by the fixed filter photometer.

Finally, upper confidence limits are established for both Q and M in order to obtain a number which represents the determination as to whether a particular piece of data is reliable or not reliable, e.g. an outlier is found permitting a geometric interpretation of Q and M, illustrated to visualize the same as a measure of distance from the multivariate mean, which is the intersection of the principal components of the data set. Q may be illustrated as a measure of distance off the plane of an ellipse encompassing the PC data, while M may be visualized as a point within the plane of such ellipse but outside the confines of such ellipse. Thus, the value of Q or M may be compared to the Q or M limits, in tabular form or graphically, to determine the existence of an outlier sample in the present system.

It may be apparent that a novel and useful system for obtaining reliable chemometric data from a sample is herein provided.

It is therefore an object of the present invention to provide a system for obtaining multivariate data from a sample which utilizes a photometer, rather than a spectrometer, and have such data confirmed as to reliability determinations.

Another object of the present invention is to provide a system for obtaining reliable property data of a chemical system which utilizes a photometer that is cheaper and more efficient to employ in chemical process analyses than prior art spectrometers.

A further object of the present invention is to provide a system for obtaining reliable property data from a chemical sample using a fixed filter photometer that is capable of determining the reliability of data utilizing the Mahalanobis distance, the sum of squares statistical and other statistical techniques.

A further object of the present invention is to provide a system for obtaining reliable property data utilizing a fixed filter photometer having means for determining outlier statistics which is relatively simple to program and use.

Another object of the present invention is to provide a system for obtaining reliable property data using a fixed filter photometer and means for predicting the reliability of the data obtained by the such photometer, in order to determine the existence of sample conditions which exceed chemometric models and permits one to operate a chemical process properly.

A further object of the present invention is to provide a system for obtaining reliable property data utilizing a fixed filter photometer operating at a plurality of discrete narrow band wavelengths which is capable of detecting abnormal temperature or pressure, the presence of bubbles, or cloudiness in a stream, contamination by an unwanted chemical species, improper flow rates, and the like.

A further object of the present invention is to provide a system for obtaining reliable property data utilizing a fixed filter photometer in order to improve chemical processing efficiency.

Another object of the present invention is to provide a system for obtaining reliable property data from a sample utilizing a fixed filter photometer in order to reduce personnel exposure to dangerous chemicals.

Yet another object of the present invention is to provide a system for obtaining reliable property data from a sample utilizing a fixed filter photometer which is capable of quickly detecting upsets in a chemical system and is capable of improving product quality from the chemical process.

A further object of the present invention is to provide a system for obtaining reliable property data from a sample which contains no moving parts and is not susceptible to misalignment, endemic to prior art spectrometers and like scanning instruments.

Another object of the present invention is to provide a system for obtaining reliable property data from a sample utilizing a fixed filter photometer for obtaining data representing a sample characteristic which overcomes the disadvantage of prior art photometers which were susceptible to masking through the introduction of contaminant species in the chemical process stream.

The invention possesses other objects and advantages especially as concerns particular characteristics and features thereof which will become apparent as the specification continues.

Figure 1:
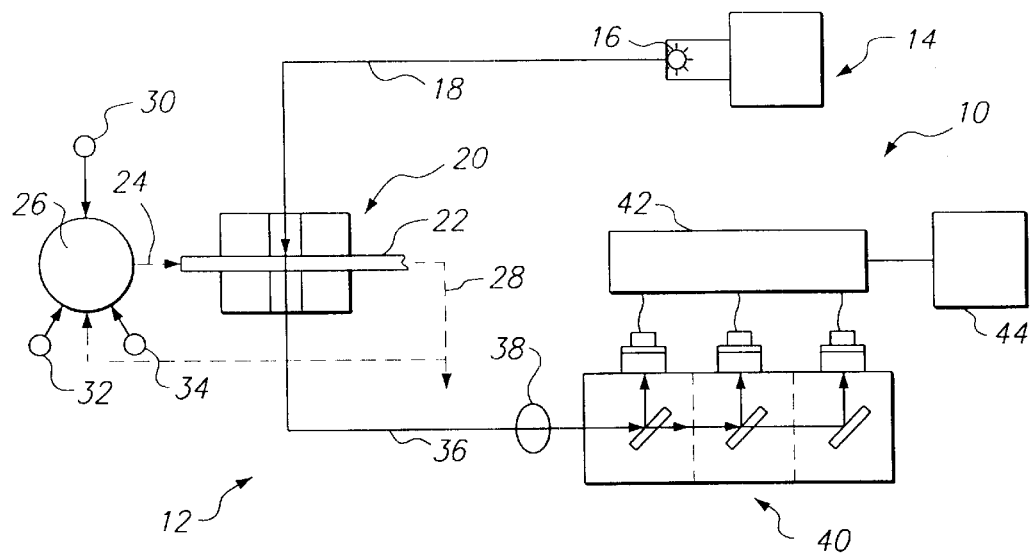
FIG. 1 is a schematic representation of a fixed filter photometer employed in the system of the present invention.

For a better understanding of the invention reference is made to the following detailed description of the preferred embodiments and examples representative of the present invention which should be referenced to the prior described drawings.

DETAILED DESCRIPTION OF THE PREFERRED EMBODIMENTS

Various aspects of the present invention will evolve from the following description of the preferred embodiments thereof which must be taken in conjunction with the herein above delineated drawings.

The system as a whole is depicted in the drawings by reference character 10. System 10 includes a photometer 12 fully described in U.S. Pat. No. 5,825,478, which is incorporated by reference, in full to this specification. However, other types of photometers may substitute for photometer 12, such as a moving filter photometer, a dispersive photometer, as well as other types of photometers. In essence, the preferred embodiment uses which photometer 12 includes an electromagnetic radiation source 14 that may be a broad wavelength band source of light 16. Radiation from source 14 passes through a fiber optic cable 18 to sensing means 20. Sample tube 22 receives a chemical sample 24 from a schematically represented chemical process 26. It should be noted that an insertion probe may also be alternatively employed, in this regard. Chemical sample 24 is illustrated as returning to chemical process 26, although such sample may be discarded according to directional arrow 28. Also shown schematically, are sample conditions 30, 32, and 34 which may take the form of temperature, pressure, contamination, obscurements, obstructions to proper flow rate, and the like. In any case, radiation from cable 18 passes through sample tube 22, is directed through fiber optic cable 36, and pass through optional lens 38. After collimation by lens 38 the electromagnetic radiation impinges detecting means 40, which uses a plurality of beam splitters and fixed filters to produce electrical signals representative of characteristics of the sample in tube 22, such as absorbance, fluorescence, turbidity, and the like. Detecting means 40 employs a plurality of distinct wavelengths through the use of a plurality of wavelength filters each having a relatively narrow bandwidth. Thus, photometer 12 utilizes distinct wavelengths, rather than a continuous spectrum or portion of a continuous spectrum employed in the prior art spectrometers. Analyzing means 42 quantifies the output signals of the detecting means 40 into a useful characteristics of the sample passing through tube 22, i.e. absorbance. Thus, through the Beer's Law relationship, concentration of a chemical entity in sample tube 22 may be determined.

Means 44 is also depicted in the drawing for determining the reliability of the data being analyzed by analyzing means 42, within photometer 12. In other words, the quality of the data obtained by photometer 12 is determined by means 44. This is important to an operator or device controlling and regulating chemical process 26. Means 44 includes the provision and utilization of a training set of data representing the chemical sample passing through sample tube 22 by varying the value of at least one, and often many, sample conditions. Variable sample conditions may take the form of changes in temperature, concentration of the entity being detected in sample tube 22, the presence of contaminants or variation in concentration of other chemical entities found in sample tube 22, and the like. Since photometer 12 is a first-order instrument, means 44 is capable of detecting "an upset" or the presence of errant data, commonly known as an "outlier". Means 44 generates a descriptive statistic such as, but not limited to, the sum of squares, Q, or the Mahalanobis distance, M. Generally, low values of Q or M indicate a reliable measurement at sample tube 22. Until now, such a determination was only available by. the use. of full or partial spectrum spectrometers. Initially, means 44 requires a training set of data that may be obtained using multiple distinct wavelengths, determined by the interference filters, by photometer 12 itself. In addition, the training set of data may be obtained by chemical means using known chemical analyses. In any case, a particular characteristic, such as absorbance, of the chemical entity passing through tube 22 is determined at multiple distinct wavelengths under a variety of sample conditions.

Q and M are calculated using a chemometric method such as principal components analysis PCA (PCA), principal components regression PCR (PCR), partial least squares PLS (PLS), and the like. Such chemometric methods determine variation in the training data set by mathematically determining factors or principal components PC (PC). These techniques rely on the eigenvector position of the covariance or correlation matrix of the training set of data. For example, rows of the data matrix may represent samples at independent narrow band wavelengths and the columns represent the analytical wavelengths or variables for a data matrix X with m rows and n columns, that has been mean centered. The covariance matrix of X is defined as:

$$\mathrm{cov}(X) = X^T X/(m-1) \tag{1}$$

using a PCA method, the data matrix decomposes into the outer product of vectors $t_1$ and $P_1$ and a residual matrix E:

$$X = t_1 p^T_1 + t_2 p^T_2 + \ldots t_K P^T_K + E \tag{2}$$

where k is less than or equal to the smaller dimension of X.

The $t_1$ are known as the "scores" and contain information on how the particular samples relate to one another. The $p_i$ are the eigenvectors of the covariance matrix known as the "loadings". The loadings contain information on how the variables, in this case the various narrow band wavelengths used in photometer 12, relate to each other. For each $p_i$ the eigenvalues (Lambda)$_i$ for each eigenvector can be calculated by:

$$\mathrm{cov}(X) p_i = (\mathrm{Lambda})_i p_i \tag{3}$$

Another way to calculate the eigenvalues and eigenvectors for a data matrix is by PCA on the mean centered data set. An outline of this method is attached hereto as Appendix 1.

It is generally possible to describe a data set with far fewer factors than original variables with no loss of information. Such data set may be shown graphically where three variables are transformed into a two Principal Component (PC) model, such that all the samples are depicted to lie in a plane. In such a case, the co-planar samples may be enclosed by a geometric figure, such as an ellipse. PC may also be utilized to describe the direction of greatest variation in the training set of data, in the case of an ellipse along the major axis of the ellipse.

The sum of squares, Q, may also be calculated which is the sum of squares of each row of E from equation (2). For the $i^{the}$ sample in X, $x_i$:

$$Q_i = e_i e_i^T = x_i (I - P_K P_K^T) x_i^T \tag{4}$$

where $e_i$ is the $i^{the}$ row of E, $P_k$ is the matrix of the first k loading vectors retained in the PCA model (where each vector is a column of $P_k$), and I is the identity matrix of appropriate size (n times n). The Q value, or statistic, is a measure of the amount of variation in each sample not captured by the k PC's retained in the model.

M represents the measure of variation within the model. In a situation where prior art full spectrophotometers were used, the entire spectrum or a portion of an entire spectrum was reduced into the corresponding PC's and the "scores" were used to calculate M. The novelty of the present invention resides in the fact that a small number of discrete wavelengths, rather than an entire spectrum reduced to scores, is employed to calculate the Mahalanobis distance M. M is calculated for the $i^{the}$ sample in a mean centered matrix, X, by the following formula:

$$D_i^2 = x_i (X^T X/(m-1))^{-1} x_i^T \tag{5}$$

Thus, for each row of X, $x_i$, is multiplied by the inverse of the covariance matrix and by the transpose of Xi. It has been found that calculating M using absorbance as a sample characteristic, works well for discrete narrow band wavelengths of fewer than 10. Using a higher number of discrete or narrow band wavelengths often causes the M calculation to become overfit and sensitive to noise.

Confidence limits are also established for both Q and M. Such limit provides a mile marker for determining when the spectral data no longer fit the predictive chemometric model. In other words, such limits determine the limits of an outlier. There are two cases for calculating confidence limits for Q. In the first case, fewer PC's than variables exist. The second case involves the number PC's equaling the number of variables. In the first case, confidence limits can be calculated for Q, provided that all the eigenvalues of the covariance matrix have been obtained. The following formulas may be used to calculate Q:

$$Q\alpha = \theta_1 [(c_\alpha (2\theta_2 h_o^2)^{1/2}/\theta_1 t1 + [\theta_2 h_o - 1)/\theta_1^2]^{1/h}{}_o \tag{6}$$

where:

$$\theta_i = \Sigma \, (\text{Lambda})_j^i \quad (7)$$

for i=1, 2, 3 and where j=k+1 to n and:

$$h_o = 1 - 2\theta_1\theta_3/3\theta_2^2 \quad (8)$$

In equation 6 $c_\alpha$ is the standard normal deviate corresponding to the $(1-\alpha)$ percentile. In equation (7), k is the number of PC's retained in the chemometric model, n is the total number of PC's, and $\text{Lambda}_j$ are the eigenvalues for each PC.

In the second case where the number of PC's equals the number of variables Q should equal 0, by definition, since all the variation in the data set must be explained by the PC's. It is also possible to detect when Q no longer equals 0. That is to say, it is possible to detect when an interference is present in a discrete wavelength employed in the system. A t-statistic based interval fulfills this determination. An upper limit is set as follows:

$$U = X_{bar} + t_{95, \, (n-1)}{}^{s/M^{1/2}} \quad (9)$$

where $X_{bar}$ is the average of the Q values from each sample of the training data set (normally near 0), s is the standard deviation of the Q value, m is the number of samples, and $T_{95}(n-1)$ is the t statistic from a statistic table.

The confidence limit for M can be calculated from the F distribution as follows:

$$D_{K1M1\alpha} = k(M-1)/(m-k)F_{K, \, M-K, \, \alpha} \quad (10)$$

where m is the number of samples in the training data set, k is the number of PC's in the model and $F_{k, \, (M-K), \, \alpha}$ derives from the F-distribution tables.

Means 44 may take the form of a microprocessor programmed to perform the above-identified calculations for Q and M. In addition, using the process above delineated, Q and M may be calculated by first performing a PCA on the training set of data through such programs as MATLAB UNSCRAMBLER, or PLS, PLUS IQ,(GALACTIC INDUSTRIES) and others. The matrix is calculated, in the present case, by using MATLAB. The eigenvalues of the covariance matrix may also be calculated utilizing MATLAB. Finally, the limits for Q may be calculated from a spread sheet or a hand calculator. M may be calculated in a similar manner. For example, a microprocessor model number PCB80C552-5-24WP manufactured by Koninklijke Phillips Electronics, Emdoven, The Netherlands, may be programmed in this manner. Appendix 2 represents the hexadecimal representations of the machine readable code, Intel format, useable in the present application.

The following examples represent further illustration of the invention of the present application, but are not deemed to restrict the invention in any manner.

EXAMPLE 1

A scanning spectrophotometer was used with five meters of 500 micron core low-OH NIR optical fibers. The samples were measured in a one centimeter quartz cuvette, in a fiber optic cell holder known as HeaterCell, available from Optical Solutions, Inc. of Folsom, Calif. The sample temperatures were controlled to better than 0.2 degrees centigrade. CAMO'S UNSCRAMBLER and Galactic Industries' PLSPlus/IQ were used for the PLS analysis of the full spectrum data which led to determination of four wavelengths for use in a filter photometer. A fixed filter photometer, known as the ChemView manufactured by Optical Solutions, Inc. of Folsom, Calif., was used with one reference wavelength and four analytical wavelengths. The fixed filter photometer transmitted absorbances from these wavelengths via 4–20 mA signals to a personal computer, which converted this information to the chemical property of percent of OH using the MLR model. In the process, an insertion probe was used through a ball valve to a process transfer pipe. The probe was connected to the filter photometer with 65 m of optical fiber cable each way, one to the light source and one to the detector. The fixed filter photometer results were trended and compared with samples analyzed by the reference method in a laboratory. It was found that changing the OH content in the NIR spectra showed variation occurring above the 1380 nm. The region near 1200 nm was identified as resulting from C—H groups in silicone. The region above 1350 nm was determined to be related to C—H and O—H groups. It was determined that temperature generally has a strong effect on the NIR spectra of water or hydroxyl groups. A four factor PLS model was obtained for experimental design. Four wavelengths were determined to be important for use with the ChemView fixed filter photometer.

EXAMPLE 2

The ChemView fixed filter photometer of Example 1 was equipped with four wavelength filters corresponding to the four particular wavelengths determined in Example 1. Namely, such peak wavelengths lie at 1180, 1380, 1460, and 1540 nanometers in the NIR region. A reference wavelength of 1300 nm was used in the ChemView as a reference wavelength. The fixed filter photometer computes absorbance (=−log [sample/reference]) since absorbance is linearly related to concentration in most applications, according to Beer's Law. The insertion probe was connected to the fixed filter photometer and the training set of data was reanalyzed. Absorbances were recorded for each of the four wavelengths and a multi linear regression (MLR) model was then developed to determine coefficient for each of the four wavelengths. The MLR calibration was accomplished through a Microsoft Excel spread sheet program. In general, the model for OH content in silicone involved multiplying the absorbance measured at each particular wavelength with its MLR coefficient, summing the products, and adding the constant term.

A ChemView fixed filter photometer was then positioned in a control room and the insertion probe was placed back into the transfer pipe. The absorbance signals from the fixed filter photometer were acquired in a personal computer, where the percent of OH was determined from the MLR model. A 4–20 mA signal scaled to OH concentration was sent from the personal computer to a process computer. OH concentration was plotted for one week and was verified by grab samples taken at certain intervals. The grab samples were generally in agreement within 0.05 percent at the different OH concentrations.

EXAMPLE 3

Figure 2:
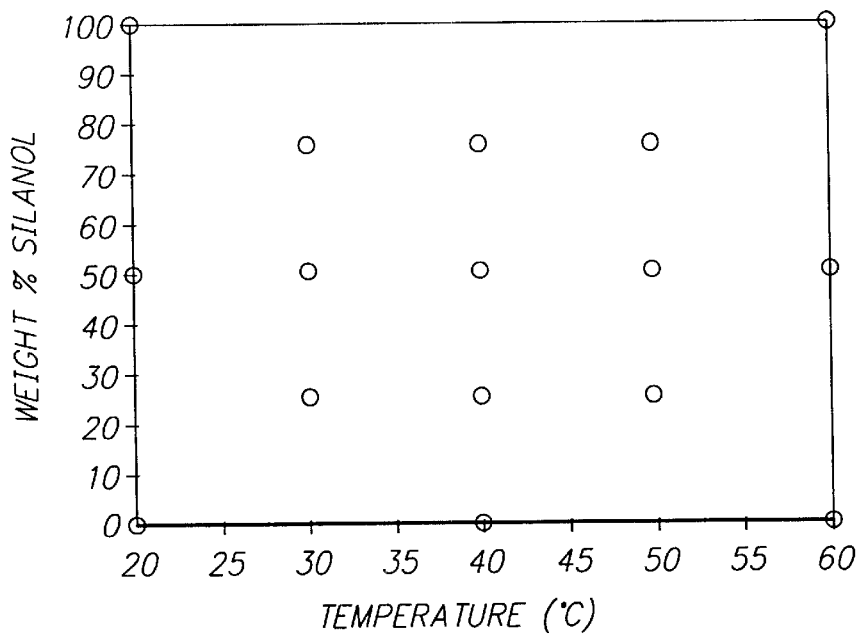
FIG. 2 is a graph representing the obtaining of training set of data employed in the example 1.

An in-situ study was undertaken to determine the accuracy of the system of the present invention by measuring silanol in an OH dilution tank. A ChemView fixed filter photometer was connected via fiber optics to a probe inserted directly into the dilution tank recirculation line. A training set of spectra were collected from a two-dimensional designed experiment, where the silanol content and temperature were varied to simulate the conditions expected in the OH dilution tank. Silanol was varied from 0 to 1.5 wt percent in 5 increments, and the temperature was varied from 20 to 60 degrees centigrade in 5 increments. A schematic of the designed experiment is shown in FIG. 2. The absorbances at 4 wavelengths (1180, 1380, 1460, and 1540 nm) were recorded, using the photometer. In addition, the absorbances were translated into predicted values and each sample was chemically analyzed for an actual value. Table I—Absorbance Data shows these results.

TABLE I

Absorbance Data

| Sample | Absorbance Wavelength (NM) | | | | Concentrations | | Statistics (M and Q) | |
|---|---|---|---|---|---|---|---|---|
| | 1180 | 1380 | 1460 | 1540 | Lab | Predicted | M lim 11.45 | Q lim 31.70 |
| 0% 16C | 421 | 293 | 73 | 196 | 0 | 86 | 5.44 | 0.18 |
| 50% 16C | 415 | 398 | 92 | 220 | 7858 | 7811 | 2.65 | 0.33 |
| 100% 16C | 411 | 418 | 114 | 265 | 15716 | 15696 | 13.27 | 2.86 |
| 25% 30C | 411 | 373 | 80 | 200 | 3929 | 3970 | 1.46 | 0.24 |
| 50% 30C | 410 | 418 | 90 | 214 | 7858 | 7778 | 1.19 | 0.25 |
| 75% 30C | 408 | 442 | 101 | 232 | 11787 | 11656 | 1.52 | 0.48 |
| 0% 40C | 409 | 287 | 71 | 192 | 0 | 70 | 4.32 | 0.68 |
| 25% 40C | 407 | 379 | 78 | 198 | 3929 | 3895 | 1.27 | 0.46 |
| 50% 40C | 405 | 434 | 88 | 210 | 7858 | 7826 | 0.57 | 0.08 |
| 75% 40C | 404 | 464 | 100 | 227 | 11787 | 11841 | 1.74 | 0.88 |
| 100% 40C | 403 | 483 | 112 | 247 | 15716 | 15861 | 5.29 | 1.84 |
| 25% 50C | 403 | 383 | 77 | 196 | 3929 | 3922 | 1.99 | 0.72 |
| 50% 50C | 401 | 448 | 87 | 207 | 7858 | 7998 | 1.37 | 0.28 |
| 75% 50C | 399 | 487 | 97 | 219 | 11787 | 11557 | 2.13 | 0.55 |
| 0% 60C | 400 | 280 | 69 | 189 | 0 | −75 | 10.86 | 0.68 |
| 50% 60C | 397 | 460 | 85 | 203 | 7858 | 7889 | 3.93 | 1.20 |
| 100% 60C | 393 | 541 | 107 | 232 | 15716 | 15806 | 5.00 | 0.57 |

The Q and M statistics were then calculated by first mean centering the absorbance data of Table I using the column means calculated for each variable (wavelength). Table II—Q and M Calculations, shows the summary of these calculations.

TABLE II

Q and M Calculations

Column means

| 406 | 411 | 89 | 215 |
|---|---|---|---|

Inverse covariance matrix -

| 7.3152e-3 | 7.6960e-4 | −3.7983e-3 | −1.7143e-3 |
|---|---|---|---|
| 7.6960e-4 | 3.6230e-4 | −5.7315e-3 | 2.7486e-3 |
| −3.7983e-3 | −5.7315e-3 | .14474 | −.081322 |
| −1.7143e-3 | 2.7486e-3 | −.081322 | .050155 |

$D^2_{3,17,.05} = 3(17-1)/\text{Mahalanobis Distance}$ Limit Calculation (Eq.10)

Eigenvalues calculated for training set data
Eigenvectors calculated for training set data

| $P_1$ | $P_2$ | $P_3$ | $P_4$ |
|---|---|---|---|
| −.05141 | .18136 | −.98207 | −.00235 |
| .96944 | −.22119 | −.09172 | .05339 |
| .15398 | .43039 | .07353 | −.88636 |
| .18394 | .85612 | .14737 | .45989 |

$(I-P_k P_k^T)$ matrix

| 1.6694e-4 | 4.2797e-4 | −.011193 | 6.4371e-3 |
|---|---|---|---|
| 4.2797e-4 | 1.0962e-3 | −.028680 | .016493 |
| −.011193 | −.028680 | .75051 | −.43161 |
| 6.4371e-3 | .016493 | −.43161 | .24822 |

Q limit calculation (Eq. 6–8)
Calibration Coefficients
b0=−7664.94
b1=−63.85
b2=23.25
b3=148.41
b4=86.67

The inverse covariance matrix was calculated using equation (1) of the above specification and is depicted in Table II. The eigenvalues and loadings (eigenvectors) were calculated using PCA as outlined in Appendix I. These values are also shown on Table II. Thus, this experiment involved three factors which were retained in the model. The matrix $(I-P_k^T)$ was calculated based on three retained eigenvectors and is summarized on Table II. Table II also shows the PLS calibration coefficients for the particular silanol analysis undertaken.

Figure 3:
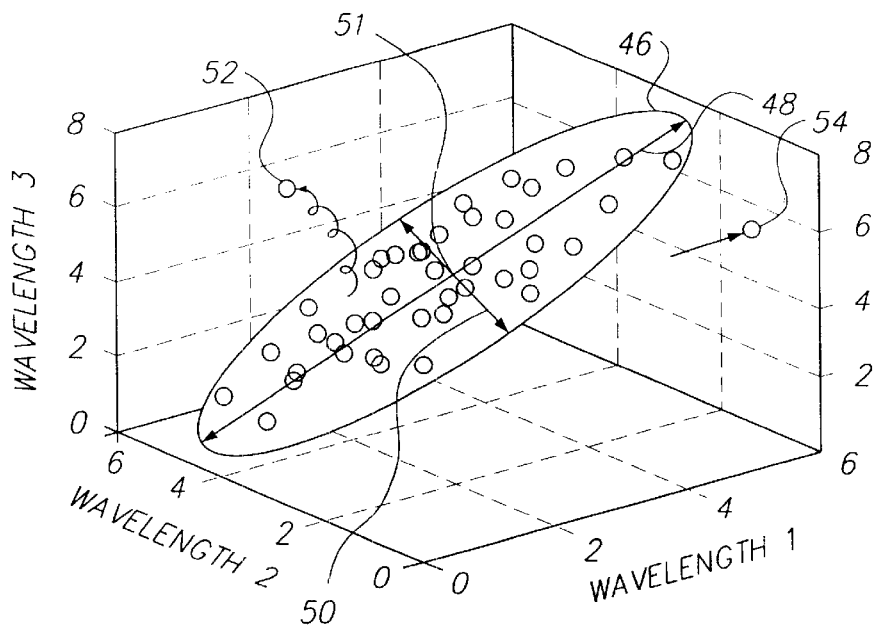
FIG. 3 is a schematic representation of principal component data typical of the system of the present invention.

Table I also summarizes the Q and M statistics in relation to each set of data obtained. The limit for Q, based on three factors and a fourth eigenvalue of 18, calculated using equations (6)–(8) was 31.7. The M limit calculated using equation (10) was 11.4. The values for Q and M were small because, since the samples employed were also the training set of data. The sample with 100 percent OH at 16 degrees centigrade appeared to be outlier, but is deemed to be within the scope of the experiment shown on FIG. 2. FIG. 3 is a graphical representation of an experiment such as that shown in Example 2 in which three variables are measured on the data set. All samples generally lie in a plane and may be enclosed by an ellipse 46. It is also apparent that there is more variation along axis 48 than axis 50 of the ellipse 46. It may be said that the first factor or PC describes the direction of greatest variation in the data set, which is major axis 48 of the ellipse. The second PC aligns with the greatest amount of variation that is orthogonal to the first PC, along minor axis 50 of ellipse 46. The intersection of axes 48 and 50 indicates the multivariate mean 51. It should also be noted that outlier sample 52 is calculated according to the sum of squares, Q and lies outside the plane of ellipse 46. Another outlier 54 lies within the plane of ellipse 46 but is found outside the confines of ellipse 46 and is calculated by using the Mahalanobis distance, M. The axis of the schematic depicted in FIG. 3 represent three different wavelengths utilized by the fixed filter photometer to obtain the data samples.

EXAMPLE 4

The model parameters of Example 3 were run on the next day from that of Example 3. Table III shows the results which indicates that the predicted values were well within the error of the calibration, and Q and M values were well below the limits delineated in Example 3. This example indicates that the fixed filter photometer employed is stable from day to day during normal operations on samples within the experimental design.

TABLE III

Test Samples for Silanol Analysis
Model Parameters - Run on Next Day

| Sample | Absorbance | | | | Actual | Predicted | D2 | Q |
|---|---|---|---|---|---|---|---|---|
| | 1180 | 1380 | 1460 | 1540 | | | | |
| 30% 60C | 397 | 401 | 78 | 197 | 4715 | 4958 | 5.38 | 1.88 |
| 60% 35C | 408 | 435 | 94 | 219 | 9430 | 9330 | 1.44 | .71 |
| 30% 25C | 414 | 379 | 83 | 204 | 4715 | 4710 | 3.45 | .96 |
| 30% 18C | 417 | 373 | 85 | 207 | 4715 | 4936 | 7.20 | 2.85 |

TABLE III-continued

Test Samples for Silanol Analysis
Model Parameters - Run on Next Day

| Sample | Absorbance | | | | Actual | Predicted | D2 | Q |
|---|---|---|---|---|---|---|---|---|
| | 1180 | 1380 | 1460 | 1540 | | | | |
| 60% 18C | 415 | 404 | 96 | 228 | 9430 | 9237 | 2.39 | .014 |
| 80% 18C | 415 | 414 | 106 | 245 | 12573 | 12427 | 4.76 | .39 |

EXAMPLE 5

Water was included as a dimension in the designed experiment in addition to the variation of OH concentration and temperature. The presence of water was varied between medium (M) and high values (H) with increasing silanol content. The temperature was also varied over the range of the first design. experiment depicted in Example 3. The high water samples were used as training data samples that were equilibrated with liquid water for 24 hours. The medium water samples were 50—50 mixtures of high and no waste samples. No attempt was made to determine the water content other than to note that it was either at a medium (M) or high (H) level. It was found that both Q and M were sensitive to interference by water particularly in the high silanol high water samples. Excursions of M above its limits were seen for most of the samples. Q values. above the limit were also noted. The results of this test are found in Table IV.

TABLE IV

Water Upset M = Medium, H = High

| Sample | Absorbance | | | | Actual | Predicted | D2 | Q |
|---|---|---|---|---|---|---|---|---|
| | 1180 | 1380 | 1460 | 1540 | | | | |
| 0% M16C | 420 | 294 | 75 | 196 | 0 | 470 | 10.47 | 4.48 |
| 0% H16C | 416 | 293 | 75 | 196 | 0 | 702 | 9.24 | 4.75 |
| 50% M16C | 418 | 395 | 95 | 222 | 7858 | 8167 | 12.02 | 6.09 |
| 50% H16C | 415 | 395 | 97 | 224 | 7858 | 8829 | 16.80 | 11.07 |
| 100% M16C | 412 | 424 | 120 | 266 | 15716 | 16748 | 20.77 | 8.10 |
| 100% H16C | 410 | 427 | 128 | 269 | 15716 | 18393 | 106.0 | 70.54 |
| 0% M40C | 411 | 286 | 73 | 194 | 0 | 388 | 7.02 | 2.94 |
| 0% H40C | 407 | 289 | 75 | 194 | 0 | 1010 | 19.01 | 11.10 |
| 50% M40C | 407 | 432 | 91 | 211 | 7858 | 8183 | 6.03 | 4.14 |
| 50% H40C | 406 | 432 | 95 | 215 | 7858 | 9187 | 18.57 | 13.93 |
| 100% M40C | 403 | 485 | 119 | 251 | 15716 | 17293 | 45.71 | 31.47 |
| 100% H40C | 402 | 483 | 127 | 255 | 15716 | 18844 | 165.4 | 120.3 |
| 0% M60C | 399 | 280 | 71 | 190 | 0 | 0 | 17.37 | 4.53 |
| 0% H60C | 402 | 285 | 72 | 190 | 0 | 0 | 17.59 | 7.50 |
| 50% M60C | 397 | 459 | 86 | 203 | 7858 | 8014 | 2.31 | .028 |
| 50% H60C | 397 | 460 | 93 | 208 | 7858 | 9509 | 19.87 | 13.68 |
| 100% M60C | 394 | 543 | 113 | 234 | 15716 | 16852 | 37.46 | 25.26 |
| 100% H60C | 393 | 50 | 124 | 241 | 15716 | 19085 | 187.1 | 137.2 |

EXAMPLE 6

The temperature range of the designed experiment of Example 3 was broadened from 20 to 120 degrees centigrade in five increments. The M value for samples above the 60 degree limit of the designed experiment well exceeded such limit. The Q values however only exceeded the limit with the samples above 120 degrees centigrade. Thus, it was found that M was very sensitive to temperature excursions out of the bounds of the experimental design, while Q is not as sensitive to temperature excursions. Table V represents the results of this Example.

TABLE V

Temperature Excursion

| Sample | Absorbance | | | | Actual | Predicted | D2 | Q |
|---|---|---|---|---|---|---|---|---|
| | 1180 | 1380 | 1460 | 1540 | | | | |
| 0% 20C | 416 | 291 | 72 | 196 | 0 | 210 | 3.25 | .168 |
| 50% 20C | 413 | 401 | 89 | 219 | 7858 | 7476 | 5.54 | 3.16 |
| 100% 20C | 408 | 426 | 113 | 263 | 15716 | 15751 | 14.55 | 4.32 |
| 25% 45C | 404 | 379 | 77 | 197 | 3929 | 3851 | 2.43 | 1.20 |
| 75% 45C | 400 | 473 | 100 | 223 | 11787 | 11959 | 7.95 | 5.29 |
| 0% 70C | 393 | 275 | 70 | 191 | 0 | 577 | 22.36 | 1.14 |
| 50% 70C | 390 | 467 | 82 | 201 | 7858 | 7879 | 19.47 | 10.18 |
| 100% 70C | 388 | 564 | 105 | 255 | 15716 | 15756 | 8.52 | .967 |
| 25% 95C | 379 | 382 | 72 | 191 | 3929 | 4255 | 38.58 | 8.25 |
| 75% 95C | 378 | 551 | 85 | 202 | 11787 | 11130 | 56.73 | 29.92 |
| 0% 120C | 370 | 257 | 65 | 182 | 0 | 105 | 86.46 | 3.21 |
| 50% 120C | 367 | 480 | 75 | 192 | 7858 | 7831 | 86.28 | 34.82 |
| 100% 120C | 367 | 642 | 87 | 202 | 15716 | 14245 | 130.8 | 73.14 |

EXAMPLE 7

Figure 4:
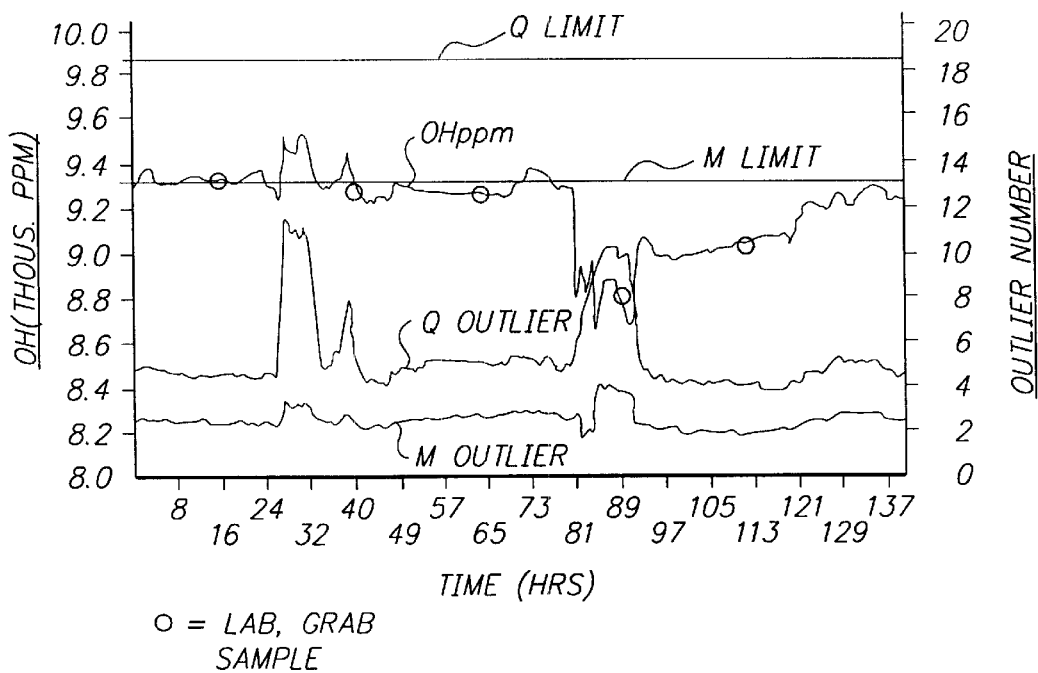
FIG. 4 is a graph representing a detection of the concentration of hydroxide in the M and Q statistics over an approximately 7 day period of time, according to Example 5.

The ChemView fixed filter photometer analyzer system was further demonstrated by attaching the probes of the fixed filter photometer directly to the OH dilution tank recirculation line. This allowed direct analysis of the dilutions made in the tank and also provided a look into the effect of water and temperature on the on-line analysis using Q and M. FIG. 4 represents a multi-day trend of the silanol analysis results using the system of the present invention. An expanded temperature designed experiment model was employed for the analysis of Example 7. Thus, the Q and M limits were slightly different from those of Examples 3–6 noted in Example 3. Structure in the silanol analysis is noted at about the 24 hour period and is due to a water upset in the process line. The Q and M trends reflect this, although neither statistic exceeds its particular limit. It should be noted that the Q and M limits may be tightened by going to a 1 sigma rather than a 2 sigma limit shown in Example 7. At the beginning of the third day, a new dilution was made. The higher water levels, and lower OH levels, can be viewed in the increase of the Q and M outliers. Subsequent to this time, cycling the process stream through sieve beds decreased the Q and M outliers. The circles appearing on the OH ppm line indicate grab samples which, through chemical analysis, confirm the accuracy of the data obtained by the system of the present invention.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A system for obtaining reliable chemometric data from a sample including components from a chemical process under at least one variable sample condition, comprising:

a. a fixed filter photometer for obtaining data representing a sample characteristic by interacting at least a first beam of electromagnetic radiation at a first wavelength possessing a narrow band width, and a second beam of electromagnetic radiation at a second wavelength possessing a narrow bandwidth, said first and second wavelengths relating to components in the sample; and b. means for determining the reliability of said data representing a sample characteristic, said means utilizing a training set of data representing said sample characteristic being repeatedly determined by varying the value of at least one sample condition at said first and second wavelengths, a mean center of said training set of data at said first and second wavelengths, and a number representing the amount of variation between said mean center of said training set of data and said data representing a sample characteristic, to determine outliers of said data representing a sample characteristic.

2. The system of claim 1 in which said number representing said amount of variation comprises a Mahalanobis distance.

3. The system of claim 1 in which said number representing an amount of variation comprises a sum of square error.

4. The system of claim 1 in which said means for determining the reliability of said data representing a sample characteristic further comprises a limit for said number representing an amount of variation.

5. The system of claim 4 in which said number representing said amount of variation comprises a Mahalanobis distance.

6. The system of claim 5 in which said number representing an amount of variation comprises a sum of squares error.

7. A method of obtaining reliable chemometric data from a sample including components from a chemical process, under at least one variable sample condition, comprising:

a. obtaining data representing a sample characteristic by utilizing a fixed filter photometer to generate and to interact with the sample at least a first beam of electromagnetic radiation at a first wavelength possessing a narrow bandwidth, and a second beam of electromagnetic radiation at a second wavelength possessing a narrow bandwidth, said first and second wavelengths relating to components in the sample;

b. determining the reliability of said data representing a sample characteristic utilizing a training set of data representing said sample characteristic being repeatedly determined by varying the value of at least one sample condition at said first and second wavelengths, mean centering said training set of data at said first and second wavelengths, and calculating a number representing the amount of variation between said mean center of said training set of data and said data representing a sample characteristic, to determine outliers of said data representing a sample characteristic.

8. The method of claim 7 which further comprises determining a limit for said number representing an amount of variation between said mean center of said training set of data and said data representing a sample characteristic.

9. The method of claim 7 in which said number representing said amount of variation comprises a Mahalanobis distance.

10. The method of claim 7 in said which said number representing said amount of variation comprises a sum of square error.

11. The method of claim 9 which further comprises determining a limit for said number representing an amount of variation between said mean center of said training set of data and said data representing a sample characteristic.

12. The method of claim 10 in which said number representing said amount of variation comprises a Mahalanobis distance.

13. A system for obtaining reliable chemometric data from a sample including components from a chemical process under at least one variable sample condition, comprising:

a. a photometer for obtaining data representing a sample characteristic by interacting electromagnetic radiation with the sample and analyzing said interaction at least at a first wavelength possessing a narrow bandwidth, and a second wavelength possessing a narrow bandwidth, said first and second wavelengths relating to components in the sample; and b. means for determining the reliability of said data representing a sample characteristic, said means utilizing a training set of data representing said sample characteristic being repeatedly determined by varying the value of at least one sample condition at said first and second wavelengths, a mean center of said training set of data at said first and second wavelengths, and a number representing the amount of variation between said mean center of said training set of data and said data representing a sample characteristic, to determine outliers of said data representing a sample characteristic.

14. The system of claim 13 in which said number representing said amount of variation comprises a Mahalanobis distance.

15. The system of claim 14 in which said number representing an amount of variation comprises a sum of square error.

16. The system of claim 5 in which said means for determining the reliability of said data representing a sample characteristic further comprises a limit for said number representing an amount of variation.

17. A method of obtaining reliable chemometric data from a sample including components in a chemical process, under at least one variable sample condition, comprising:

a. obtaining data representing a sample characteristic by utilizing a photometer to generate and to interact with the sample at least a first beam of electromagnetic radiation at a first wavelength possessing a narrow bandwidth, and a second beam of electromagnetic radiation at a second wavelength possessing a narrow bandwidth, said first and second wavelengths relating to components in the sample;

b. determining the reliability of said data representing a sample characteristic utilizing a training set of data representing said sample characteristic being repeatedly determined by varying the value of at least one sample condition at said first and second wavelengths, mean centering said training set of data at said first and second wavelengths, and calculating a number representing the amount of variation between said mean center of said training set of data and said data representing a sample characteristic, to determine outliers of said data representing a sample characteristic.

18. The method of claim 17 which further comprises determining a limit for said number representing an amount of variation between said mean center of said training set of data and said data representing a sample characteristic.

19. The method of claim 17 in which said number representing said amount of variation comprises a Mahalanobis distance.

20. The method of claim 17 in said which said number representing said amount of variation comprises a sum of squares error.

* * * * *